US006930183B2

(12) United States Patent
Duyck et al.

(10) Patent No.: US 6,930,183 B2
(45) Date of Patent: Aug. 16, 2005

(54) ALKYLATED IMINODIBENZYLS AS ANTIOXIDANTS

(75) Inventors: Karl J. Duyck, Waterbury, CT (US); Theodore E. Nalesnik, Hopewell Junction, NY (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 10/417,861

(22) Filed: Apr. 17, 2003

(65) Prior Publication Data

US 2004/0214813 A1 Oct. 28, 2004

(51) Int. Cl.⁷ .......................................... C07D 223/18
(52) U.S. Cl. ...................................................... 540/588
(58) Field of Search ........................................ 540/588

(56) References Cited

U.S. PATENT DOCUMENTS

| | | | | |
|---|---|---|---|---|
| 2,764,580 A | * | 9/1956 | Schindler et al. | 540/588 |
| 2,943,112 A | | 6/1960 | Popoff et al. | 260/576 |
| 3,056,775 A | * | 10/1962 | Schindler | 540/588 |
| 3,452,056 A | | 6/1969 | Sundholm | 260/390 |
| 3,496,230 A | | 2/1970 | Kaplan | 260/576 |
| 4,013,639 A | | 3/1977 | Kitamura et al. | |
| 4,824,601 A | | 4/1989 | Franklin | 252/401 |
| 5,498,809 A | | 3/1996 | Emert et al. | 585/13 |
| 5,672,752 A | | 9/1997 | Lai et al. | 564/409 |
| 5,750,787 A | | 5/1998 | Lai et al. | 564/409 |
| 6,204,412 B1 | | 3/2001 | Lai | 564/409 |
| 6,315,925 B1 | | 11/2001 | Aebli et al. | 252/401 |
| 6,355,839 B1 | | 3/2002 | Onopchenko | 564/409 |

FOREIGN PATENT DOCUMENTS

| | | | |
|---|---|---|---|
| DE | 1142870 | | 1/1963 |
| GB | 1046353 | * | 10/1966 |
| GB | 1149508 | | 4/1969 |
| GB | 1321589 | | 6/1973 |

OTHER PUBLICATIONS

GB 792615, published Apr. 2, 1958 (Abstract).*

* cited by examiner

*Primary Examiner*—Bruck Kifle
(74) *Attorney, Agent, or Firm*—Michael P. Dilworth

(57) ABSTRACT

Disclosed herein is an antioxidant that is an alkylated iminodibenzyl of the general formula:

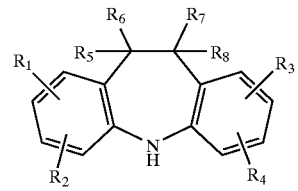

wherein:

$R_1$, $R_2$, $R_3$, and $R_4$ are independently selected from the group consisting of hydrogen, alkyl moieties, and alkenyl moieties; and $R_5$, $R_6$, $R_7$, and $R_8$ are independently selected from the group consisting of hydrocarbyl moieties and hydrogen.

9 Claims, No Drawings

ALKYLATED IMINODIBENZYLS AS ANTIOXIDANTS

BACKGROUND OF THE INVENTION

1. Field of the Invention

The present invention relates to additives for stabilizing organic products that are subjected to oxidative, thermal, and/or light-induced degradation. More particularly, the present invention relates to a class of antioxidants that are derived from the alkylation of iminodibenzyl with a suitable olefin in the presence of an acidic catalyst.

The additives can be added to numerous organic products widely used in engineering, for example, lubricants, hydraulic fluids, metal-working fluids, fuels, or polymers, to improve their performance properties.

2. Description of Related Art

U.K. Patent No. 1,046,353 discloses a composition comprising a synthetic lubricant susceptible to oxidative deterioration and as antioxidant a compound of the formula A-NH-B, wherein A is a phenyl group containing a tertiary alkyl substituent group having from 4 to 12 carbon atoms and B is phenyl or a naphthyl group.

U.K. Patent No. 1,149,508 discloses N-amino-2,8-dimethyl-iminobenzyl, its acid addition salts, and methods for preparing them. The compounds are said to be useful as starting materials in the manufacture of other iminodibenzyl derivatives.

U.S. Pat. No. 2,943,112 describes anti-oxidants from the group of the alkylated diphenylamines that are prepared by reaction of diphenylamine with alkenes in the presence of mineral acids and large quantities of acid clays as catalysts.

U.S. Pat. No. 3,496,230 describes the preparation of a mixture of 80% dinonyldiphenylamine and 15% nonyl-diphenylamine in the presence of Friedel-Crafts catalysts of the aluminum chloride type.

U.S. Pat. No. 4,824,601 discloses a process for the production of a liquid antioxidant composition by reaction of diphenylamine with diisobutylene comprising reacting diphenylamine with diisobutylene in a molar ratio of from 1:1.1 to 1:2.5 and in the presence of an acid activated earth catalyst, while ensuring that the concentration of diisobutylene remains substantially constant throughout the reaction period at a reaction temperature of at least 160° C., the reaction being effected for such a period that the content of 4,4'-dioctyldiphenylamine in the reaction mass, excluding catalyst, is below 25% by weight; and removing catalyst and unreacted diisobutylene. The use of this product as a stabilizer for organic material against oxidative degradation is also disclosed.

U.S. Pat. No. 6,315,925 discloses a mixture of nonylated diphenylamines, especially dinonylated diphenylamines, and a technically advantageous methodological process for the preparation of that mixture by using acid catalysts in small quantities. The mixture is used as an additive for stabilizing organic products that are subjected to oxidative, thermal, and/or light-induced degradation.

U.S. Pat. No. 6,355,839 discloses a process for the preparation of alkylated diphenylamine antioxidants that comprises alkylating diphenylamine with a polyisobutylene in the presence of a clay catalyst, wherein the polyisobutylene has an average molecular weight in the range of 120 to 600 and wherein the polyisobutylene contains at least 25% methylvinylidene isomer.

The disclosures of the foregoing are incorporated herein by reference in their entirety.

SUMMARY OF THE INVENTION

One object of the present invention is to provide novel iminodibenzyl compositions.

Another object of the present invention is to provide a lubricant additive effective for imparting antioxidant properties to a lubricating oil, fuel composition, or rubber formulation.

These and other objects are achieved by the present invention, which is related to a class of lubricant additives that is derived from the alkylation of iminodibenzyl with a suitable olefin in the presence if an acidic catalyst. The additives are defined by the general formula:

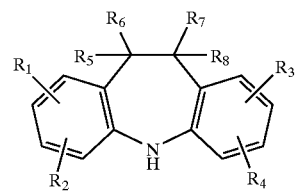

wherein:

$R_1$, $R_2$, $R_3$, and $R_4$ are independently selected from the group consisting of hydrogen, alkyl moieties, and alkenyl moieties; and $R_5$, $R_6$, $R_7$, and $R_8$ are independently selected from the group consisting of hydrocarbyl moieties and hydrogen.

Such compounds may have useful antioxidant properties for use as antioxidants in compounded tires, polyols, plastics, urethanes, greases, motor oils, rubber belts, cables, gaskets, seals, rubber products in the garment and carpet industries.

More particularly, the present invention is directed to an alkylated iminodibenzyl of the general formula:

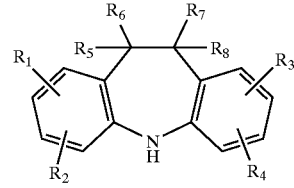

wherein:

$R_1$, $R_2$, $R_3$, and $R_4$ are independently selected from the group consisting of hydrogen, alkyl moieties, and alkenyl moieties; and $R_5$, $R_6$, $R_7$, and $R_8$ are independently selected from the group consisting of hydrocarbyl moieties and hydrogen.

In another aspect, the present invention is directed to a composition comprising:

A) an organic product selected from the group consisting of lubricants, hydraulic fluids, metal-working fluids, fuels, and polymers; and B) a stabilizing amount of an alkylated iminodibenzyl of the general formula:

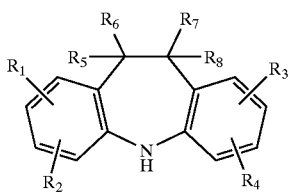

wherein:
R$_1$, R$_2$, R$_3$, and R$_4$ are independently selected from the group consisting of hydrogen, alkyl moieties, and alkenyl moieties; and
R$_5$, R$_6$, R$_7$, and R$_8$ are independently selected from the group consisting of hydrocarbyl moieties and hydrogen.

In still another aspect, the present invention is directed to a method for inhibiting the oxidation of an organic product selected from the group consisting of lubricants, hydraulic fluids, metal-working fluids, fuels, and polymers comprising adding to said product a stabilizing amount of an alkylated iminodibenzyl of the general formula:

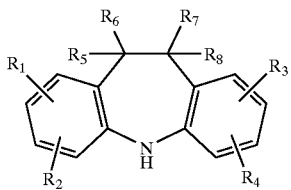

wherein:
R$_1$, R$_2$, R$_3$, and R$_4$ are independently selected from the group consisting of hydrogen, alkyl moieties, and alkenyl moieties; and
R$_5$, R$_6$, R$_7$, and R$_9$ are independently selected from the group consisting of hydrocarbyl moieties and hydrogen.

DESCRIPTION OF THE PREFERRED EMBODIMENTS

As noted above, the present invention relates to a class of lubricant additives defined by the general formula:

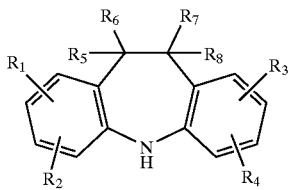

wherein:
R$_1$, R$_2$, R$_3$, and R$_4$ are independently selected from the group consisting of hydrogen, alkyl moieties, and alkenyl moieties; and
R$_5$, R$_6$, R$_7$, and R$_8$ are independently selected from the group consisting of hydrocarbyl moieties and hydrogen.

Where R$_1$, R$_2$, R$_3$, and R$_4$ are alkyl or alkenyl moieties, it is preferred that such moieties comprise from 3 to 32 carbon atoms.

When R$_1$, R$_2$, R$_3$, and/or R$_4$ are alkyl, they can, for example be propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, isomers of the foregoing, and the like.

When R$_1$, R$_2$, R$_3$, and/or R$_4$ are alkenyl, they can, for example be propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, hentriacontenyl, dotriacontenyl, isomers of the foregoing, and the like.

R$_5$, R$_6$, R$_7$, and/or R$_8$ can be hydrogen or hydrocarbyl moieties. Where R$_5$, R$_6$, R$_7$, and/or R$_8$ are hydrocarbyl moieties, it is preferred that such moieties comprise from 1 to 20 carbon atoms.

As employed herein, the term "hydrocarbyl" includes hydrocarbon as well as substantially hydrocarbon groups. "Substantially hydrocarbon" describes groups that contain heteroatom substituents that do not alter the predominantly hydrocarbon nature of the group. Examples of hydrocarbyl groups include the following:

(1) hydrocarbon substituents, i.e., aliphatic (e.g., alkyl or alkenyl), alicyclic (e.g., cycloalkyl, cycloalkenyl) substituents, aromatic substituents, aromatic-, aliphatic-, and alicyclic-substituted aromatic substituents, and the like, as well as cyclic substituents wherein the ring is completed through another portion of the molecule (that is, for example, any two indicated substituents may together form an alicyclic radical);

(2) substituted hydrocarbon substituents, i.e., those substituents containing non-hydrocarbon groups which, in the context of this invention, do not alter the predominantly hydrocarbon nature of the substituent; those skilled in the art will be aware of such groups (e.g., halo, hydroxy, mercapto, nitro, nitroso, sulfoxy, etc.);

(3) heteroatom substituents, i.e., substituents that will, while having a predominantly hydrocarbon character within the context of this invention, contain an atom other than carbon present in a ring or chain otherwise composed of carbon atoms (e.g., alkoxy or alkylthio). Suitable heteroatoms will be apparent to those of ordinary skill in the art and include, for example, sulfur, oxygen, nitrogen, and such substituents as, e.g., pyridyl, furyl, thienyl, imidazolyl, etc. Preferably, no more than about 2, more preferably no more than one, hetero substituent will be present for every ten carbon atoms in the hydrocarbyl group. Most preferably, there will be no such heteroatom substituents in the hydrocarbyl group, i.e., the hydrocarbyl group is purely hydrocarbon.

In the formula described above, where any one or more of R$_5$, R$_6$, R$_7$, and/or R$_8$ is hydrocarbyl, examples thereof include, but are not limited to, unsubstituted phenyl;

phenyl substituted with one or more alkyl groups, such as methyl, ethyl, propyl, butyl, pentyl, hexyl, heptyl, octyl, nonyl, decyl, isomers of the foregoing, and the like;

phenyl substituted with one or more alkoxy groups, such as methoxy, ethoxy, propoxy, butoxy, pentoxy, hexoxy, heptoxy, octoxy, nonoxy, decoxy, isomers of the foregoing, and the like;

phenyl substituted with one or more alkyl amino or aryl amino groups;

naphthyl and alkyl substituted naphthyl;

straight chain or branched chain alkyl or alkenyl groups preferably containing from one to twenty carbon atoms, including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, oleyl, nonadecyl, eicosyl, isomers of the foregoing, and the like; and cyclic alkyl groups, such as cyclopentyl, cyclohexyl, cycloheptyl, cyclooctyl, and cyclododecyl.

The alkylated iminodibenzyls of the present invention are preferably prepared by the alkylation of iminodibenzyl in the presence of an acidic catalyst. Preferably, the acid catalyst is a clay. The use of clay as a catalyst in the alkylation of diphenylamine is disclosed in U.S. Pat. No. 3,452,056, which describes the alkylation of diphenylamine with alpha-methylstyrene and related olefins using clay as the catalyst. In U.S. Pat. No. 2,943,112 and elsewhere, clay is described as having several advantages including, for example: (1) it provides a lighter colored product, (2) it can easily be removed by filtration after the reaction, and (3) it provides a lower degree of yellow color in the alkylated product. As a catalyst, clay and other Lewis Acids, such as $AlCl_3$ or $BF_3$ are generally taught as being interchangeable. (See, U.S. Pat. Nos. 3,452,056 and 5,672,752). More recently, U.S. Pat. Nos. 5,672,752; 5,750,787; and 6,204,412 identify certain commercially available clay catalysts, including: Filtrol™ and Retrol™ available from Engelhard; Fulcat™ 14, Fulmont™ 700C, Fulmont™ 237, and Fulcat™ 22B available from Laporte Industries; and Katalysator™ K10 available from Sud-Chemi. These clays may include acid activated or acid leached clays. The clay catalysts may contain some water as received. Removal of the water prior to use may result in a lighter colored reaction product; therefore, it is desirable to use clay with low water content or remove the water by heating the clay with a nitrogen sweep or with vacuum stripping. Acid activated clays are preferred; however, Lewis Acids such as $AlCl_3$ or $BF_3$, and $BF_3$ complexes of diethyl ether, phenol, including mixtures thereof with clay could be used if special circumstances warranted.

The present invention also relates to stabilizer-containing compositions comprising organic products subject to oxidative, thermal, and/or light-induced degradation and, as stabilizer, the alkylated iminodibenzyls defined above.

A particular class of organic products subject to undesirable oxidative degradation for which the mixtures of the present invention are valuable stabilizers is formed by lubricants and operational fluids based on mineral oil or synthetic lubricants or operational fluids, e.g., carboxylic acid ester derivatives, that can be used at temperatures of 200° C. and above.

The mixtures of the present invention can be used in concentrations of from about 0.05 to about 10.0% by weight, based on the material to be stabilized. Preferred concentrations are from 0.05 to 5.0% by weight, especially from 0.1 to 2.5% by weight.

Mineral and synthetic lubricating oils, lubricating greases, hydraulic fluids, and elastomers improved in this manner exhibit excellent anti-oxidation properties which become apparent through a great reduction in the ageing phenomena exhibited by the parts being protected. The compounds of the present invention are especially advantageous in lubricating oils, in which they exhibit an excellent anti-oxidation and anti-corrosion action without the formation of acid or sludge.

Examples of synthetic lubricating oils include lubricants based on: a diester of a diprotonic acid with a monohydric alcohol, e.g. dioctyl sebacate or dinonyl adipate; a triester of trimethylolpropane with a monoprotonic acid or a mixture of such acids, e.g., trimethylolpropane tripelargonate or tricaprylate or mixtures thereof; a tetraester of pentaerythritol with a monoprotonic acid or a mixture of such acids, e.g. pentaerythritol tetracaprylate; or a complex ester of monoprotonic or diprotonic acids with polyhydric alcohols, e.g., a complex ester of trimethylolpropane with caprylic and sebacic acid or of a mixture thereof.

Other synthetic lubricants are familiar to those skilled in the art and are described, for example, in "Schmiermittel Taschenbuch" (Huthig-Verlag, Heidelberg, 1974). Especially suitable, for example, are poly-α-olefins, ester-based lubricants, phosphates, glycols, polyglycols, and polyalkylene glycols.

Elastomers that can be stabilized using the compounds of the present invention are familiar to the person skilled in the art. Especially suitable are natural and synthetic rubbers, for example, polymers of butadiene and copolymers thereof with styrene or acrylonitrile, and isoprene or chloroprene polymers.

Another class of polymers to be protected is formed by polycondensates, which can be protected from oxidative and light-induced degradation both in the state of the condensed macromolecular end product and in the state of the low molecular weight starting materials by the addition of the compounds described hereinbefore. This class includes especially the polyurethanes, which can be stabilized by the addition of alkylated iminodibenzyls to, for example, the polyols on which they are based.

The compounds of the present invention can also be added to natural and synthetic organic substances that are pure monomeric compounds or mixtures thereof, for example, mineral oils, animal or vegetable oils, waxes, and fats, or oils, waxes, and fats based on synthetic esters, e.g., phthalates, adipates, phosphates, or trimellitates, and blends of synthetic esters with mineral oils in any desired weight ratios, as are used, for example, as spinning preparations, and aqueous emulsions thereof.

The compounds of the present invention can be added to natural and synthetic emulsions of natural or synthetic rubbers, e.g., natural rubber latex or latexes of carboxylated styrene/butadiene copolymers.

The additives derived from this invention can be used as a complete or partial replacement for commercially available antioxidants currently used in lubricant formulations, and they may be used in combination with other additives typically found in motor oils and fuels. When used in combination with these other additives, synergistic performance effects may also be obtained with respect to improved antioxidancy, anti-wear, and/or frictional properties. The typical additives found in motor oils and fuels are anti-wear agents, detergents, dispersants, rust inhibitors, antioxidants, anti-foamants, friction modifiers, viscosity index (VI) improvers, and pour point depressants. See, for example, U.S. Pat. No. 5,498,809 for a description of useful lubricating oil composition additives, the disclosure of which is incorporated herein by reference in its entirety.

Examples of dispersants include polyisobutylene succinimides, polyisobutylene succinate esters, Mannich Base ashless dispersants, and the like. Examples of detergents include metallic and ashless alkyl phenates, metallic and ashless sulfurized alkyl phenates, metallic and ashless alkyl sulfonates, metallic and ashless alkyl salicylates, metallic and ashless saligenin derivatives, and the like.

Examples of antioxidants include alkylated diphenylamines, N-alkylated phenylenediamines, phenyl-α-naphthylamine, alkylated phenyl-α-naphthylamine, dimethyl quinolines, trimethyldihydroquinolines and oligomeric compositions derived therefrom, hindered phenolics, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds, and the like. The following are exemplary of such additives and are commercially available from Crompton Corporation: Naugalube® 438, Naugalube 438L, Naugalube 640, Naugalube 635, Naugalube 680, Naugalube AMS, Naugalube APAN, Naugard PANA, Naugalube TMQ, Naugalube 531, Naugalube 431, Naugard® BHT, Naugalube 403, and Naugalube 420, among others.

Examples of anti-wear additives that can be used in combination with the additives of the present invention include organo-borates, organo-phosphites, organo-phosphates, organic sulfur-containing compounds, sulfurized olefins, sulfurized fatty acid derivatives (esters), chlorinated paraffins, zinc dialkyldithiophosphates, zinc diaryldithiophosphates, phosphosulfurized hydrocarbons, and the like. The following are exemplary of such additives and are commercially available from The Lubrizol Corporation: Lubrizol 677A, Lubrizol 1095, Lubrizol 1097, Lubrizol 1360, Lubrizol 1395, Lubrizol 5139, and Lubrizol 5604, among others.

Examples of friction modifiers include fatty acid esters and amides, organo molybdenum compounds, molybdenum dialkyldithiocarbamates, molybdenum dialkyl dithiophosphates, molybdenum disulfide, tri-molybdenum cluster dialkyldithiocarbamates, non-sulfur molybdenum compounds and the like. The following are exemplary of such additives and are commercially available from R.T. Vanderbilt Company, Inc.: Molyvan A, Molyvan L, Molyvan 807, Molyvan 856B, Molyvan 822, Molyvan 855, among others. The following are also exemplary of such additives and are commercially available from Asahi Denka Kogyo K.K.: SAKURA-LUBE 100, SAKURA-LUBE 165, SAKURA-LUBE 300, SAKURA-LUBE 310G, SAKURA-LUBE 321, SAKURA-LUBE 474, SAKURA-LUBE 600, SAKURA-LUBE 700, among others. The following are also exemplary of such additives and are commercially available from Akzo Nobel Chemicals GmbH: Ketjen-Ox 77M, Ketjen-Ox 77TS, among others.

An example of an anti-foamant is polysiloxane, and the like. Examples of rust inhibitors are polyoxyalkylene polyol, benzotriazole derivatives, and the like. Examples of VI improvers include olefin copolymers and dispersant olefin copolymers, and the like. An example of a pour point depressant is polymethacrylate, and the like.

As noted above, suitable anti-wear compounds include dialkyl dithiophosphates. Preferably, the alkyl groups contain an average of at least 3 carbon atoms. Particularly useful are metal salts of at least one dihydrocarbyl dithiophosphoric acid wherein the alkyl groups contain an average of at least 3 carbon atoms.

Lubricant Compositions

Compositions, when they contain these additives, are typically blended into a base oil in amounts such that the additives therein are effective to provide their normal attendant functions. Representative effective amounts of such additives are illustrated in the following table.

| Additives | Preferred Weight % | More Preferred Weight % |
| --- | --- | --- |
| V.I. Improver | 1–12 | 1–4 |
| Corrosion Inhibitor | 0.01–3 | 0.01–1.5 |
| Oxidation Inhibitor | 0.01–5 | 0.01–1.5 |
| Dispersant | 0.1–10 | 0.1–5 |
| Lube Oil Flow Improver | 0.01–2 | 0.01–1.5 |
| Detergent/Rust Inhibitor | 0.01–6 | 0.01–3 |
| Pour Point Depressant | 0.01–1.5 | 0.01–0.5 |
| Anti-foaming Agents | 0.001–0.1 | 0.001–0.01 |
| Anti-wear Agents | 0.001–5 | 0.001–1.5 |
| Seal Swell Agents | 0.1–8 | 0.1–4 |
| Friction Modifiers | 0.01–3 | 0.01–1.5 |
| Lubricating Base Oil | Balance | Balance |

When other additives are employed, it may be desirable, although not necessary, to prepare additive concentrates comprising concentrated solutions or dispersions of the subject additives of this invention, together with one or more of the other additives (the concentrate when constituting an additive mixture being referred to herein as an additive-package) whereby several additives can be added simultaneously to the base oil to form the lubricating oil composition. Dissolution of the additive concentrate into the lubricating oil can be facilitated by solvents and by mixing accompanied by mild heating, but this is not essential. The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive-packages containing active ingredients in collective amounts of, typically, from about 2.5 to about 90 percent, preferably from about 15 to about 75 percent, and more preferably from about 25 percent to about 60 percent by weight additives in the appropriate proportions with the remainder being base oil. The final formulations can typically employ about 1 to 20 weight percent of the additive-package with the remainder being base oil.

All of the weight percentages expressed herein (unless otherwise indicated) are based on the active ingredient (AI) content of the additive, and/or upon the total weight of any additive-package, or formulation, which will be the sum of the AI weight of each additive plus the weight of total oil or diluent.

In general, the compositions of the invention contain the additives in a concentration ranging from about 0.05 to about 30 weight percent. A concentration range for the additives ranging from about 0.1 to about 10 weight percent based on the total weight of the oil composition is preferred. A more preferred concentration range is from about 0.2 to about 5 weight percent. Oil concentrates of the additives can contain from about 1 to about 75 weight percent of the additive reaction product in a carrier or diluent oil of lubricating oil viscosity.

In general, the additives of the present invention are useful in a variety of lubricating oil base stocks. The lubricating oil base stock is any natural or synthetic lubricating oil base stock fraction having a kinematic viscosity at 100° C. of about 2 to about 200 cSt, more preferably about 3 to about 150 cSt, and most preferably about 3 to about 100 cSt. The lubricating oil base stock can be derived from natural lubricating oils, synthetic lubricating oils, or mixtures thereof. Suitable lubricating oil base stocks include base stocks obtained by isomerization of synthetic wax and wax, as well as hydrocracked base stocks produced by hydrocracking (rather than solvent extracting) the aromatic and polar components of the crude. Natural lubricating oils include animal oils, such as lard oil, vegetable oils (e.g., canola oils, castor oils, sunflower oils), petroleum oils, mineral oils, and oils derived from coal or shale.

Synthetic oils include hydrocarbon oils and halo-substituted hydrocarbon oils, such as polymerized and interpolymerized olefins, gas-to-liquids prepared by Fischer-Tropsch technology, alkylbenzenes, polyphenyls, alkylated diphenyl ethers, alkylated diphenyl sulfides, as well as their derivatives, analogs, homologs, and the like. Synthetic lubricating oils also include alkylene oxide polymers, interpolymers, copolymers, and derivatives thereof, wherein the terminal hydroxyl groups have been modified by esterification, etherification, etc.

Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers. Other esters useful as synthetic oils include those made from copolymers of α-olefins and dicarboxylic acids which are esterified with short or medium chain length alcohols. The following are exemplary of such additives and are commercially available from Akzo Nobel Chemicals SpA: Ketjenlubes 115, 135, 165, 1300, 2300, 2700, 305, 445, 502, 522, and 6300, among others.

Silicon-based oils, such as the polyalkyl-, polyaryl-, polyalkoxy-, or polyaryloxy-siloxane oils and silicate oils, comprise another useful class of synthetic lubricating oils. Other synthetic lubricating oils include liquid esters of phosphorus-containing acids, polymeric tetrahydrofurans, poly α-olefins, and the like.

The lubricating oil may be derived from unrefined, refined, re-refined oils, or mixtures thereof. Unrefined oils are obtained directly from a natural source or synthetic source (e.g., coal, shale, or tar and bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to unrefined oils, except that refined oils have been treated in one or more purification steps to improve one or more properties. Suitable purification techniques include distillation, hydrotreating, dewaxing, solvent extraction, acid or base extraction, filtration, percolation, and the like, all of which are well-known to those skilled in the art. Re-refined oils are obtained by treating refined oils in processes similar to those used to obtain the refined oils. These re-refined oils are also known as reclaimed or reprocessed oils and often are additionally processed by techniques for removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst. Natural waxes are typically the slack waxes recovered by the solvent dewaxing of mineral oils; synthetic waxes are typically the wax produced by the Fischer-Tropsch process. The resulting isomerate product is typically subjected to solvent dewaxing and fractionation to recover various fractions having a specific viscosity range. Wax isomerate is also characterized by possessing very high viscosity indices, generally having a VI of at least 130, preferably at least 135 or higher and, following dewaxing, a pour point of about −20° C. or lower.

The additives of the present invention are especially useful as components in many different lubricating oil compositions. The additives can be included in a variety of oils with lubricating viscosity, including natural and synthetic lubricating oils and mixtures thereof. The additives can be included in crankcase lubricating oils for spark-ignited and compression-ignited internal combustion engines. The compositions can also be used in gas engine lubricants, turbine lubricants, automatic transmission fluids, gear lubricants, compressor lubricants, metal-working lubricants, hydraulic fluids, and other lubricating oil and grease compositions. The additives can also be used in motor fuel compositions and in rubber formulations.

The advantages and the important features of the present invention will be more apparent from the following examples.

EXAMPLES

Example 1

Twenty grams (0.102 mol) of iminodibenzyl was added to six grams of Filtrol 20x and 25.62 grams (0.256 mol) of mixed nonenes. The mixture was heated to reflux and held at temperature for 18 hours. The catalyst was removed and the residual starting materials were stripped off under vacuum. The product was identified as 95% alkylated iminodibenzyl by gas chromatography.

Oxidation Test

Pressure Differential Scanning Calorimetry Test

The antioxidant properties of the reaction products were determined in the Pressure Differential Scanning Calorimetry (PDSC) Test. Testing was performed using the Mettler-Toledo DSC27HP tester, following outlined procedures. This test measures the relative Oxidation Induction Time (OIT) of antioxidants in lubricating fluids as measured in $O_2$ gas under pressure.

The sample to be tested was blended into a model fully-formulated motor oil (see Table 1) at 0.4% by weight, that did not contain antioxidant. An additional 0.1 wt. % of Solvent Neutral 150 base oil was then added along with 50 ppm ferric naphthenate. This was then compared to a sample of the base blend containing 0.5 wt. % of Solvent Neutral 150 base oil and 50 ppm ferric naphthenate. The conditions for the test are shown in Table 2. In Table 3, the numerical value of the test results (OIT, minutes) increases with an increase in effectiveness.

TABLE 1

Base Blend for PDSC Test

| Component | Weight Percent |
| --- | --- |
| Solvent Neutral 150 | 83.85 |
| Zinc Dialkyldithiophosphate | 1.01 |
| Succinimide Dispersant | 7.58 |
| Overbased Calcium Sulfonate Detergent | 1.31 |
| Neutral Calcium Sulfonate Detergent | 0.5 |
| Antioxidant | 0.0 |
| Rust Inhibitor | 0.1 |
| Pour Point Depressant | 0.1 |
| OCP VI Improver | 5.55 |

TABLE 2

PDSC Conditions

| Conditions | Setting |
| --- | --- |
| Temperature | 200° C. |
| Gas | Oxygen |
| Flow Rate | 100 mL/minute |
| Pressure | 500 psi |
| Sample Size | 1–5 mg |
| Pan (open/closed) | open |

TABLE 3

PDSC Results

| Compound | OIT |
|---|---|
| Base Blend | 5.45 |
| Example 1 | 20.77 |

In view of the many changes and modifications that can be made without departing from principles underlying the invention, reference should be made to the appended claims for an understanding of the scope of the protection to be afforded the invention.

What is claimed is:

1. A compound of the formula:

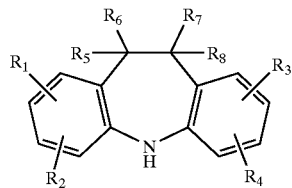

wherein:

$R_1$ is selected from the group consisting of alkenyl moieties of from 3 to 32 carbon atoms;

$R_2$, $R_3$, and $R_4$ are independently selected from the group consisting of hydrogen, alkyl moieties of from 3 to 32 carbon atoms, and alkenyl moieties of from 3 to 32 carbon atoms; and $R_5$, $R_6$, $R_7$, and $R_8$ are independently selected from the group consisting of hydrogen; unsubstituted phenyl; phenyl substituted with one or more alkyl groups; phenyl substituted with one or more alkoxy groups; phenyl substituted with one or more alkyl amino or aryl amino groups; naphthyl and alkyl substituted naphthyl; straight chain or branched chain alkyl or alkenyl groups containing from one to twenty carbon atoms; and cyclic alkyl groups.

2. The compound of claim 1 wherein $R_5$, $R_6$, $R_7$, and $R_8$ are independently selected from the group consisting of hydrogen; unsubstituted phenyl; phenyl substituted with one or more alkyl groups; phenyl substituted with one or more alkoxy groups; phenyl substituted with one or more alkyl amino or aryl amino groups; naphthyl and alkyl substituted naphthyl; straight chain or branched chain alkyl or alkenyl groups; and cyclic alkyl groups; wherein said alkyl, alkoxy, alkyl amino, alkyl substituted naphthyl and alkenyl groups are of from 1 to 20 carbon atoms.

3. A composition comprising:

A) an organic product selected from the group consisting of lubricants, hydraulic fluids, metal-working fluids, fuels, and polymers; and B) a stabilizing amount of a compound of the formula:

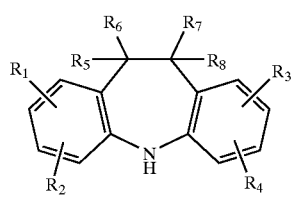

wherein:

$R_1$ is selected from the group consisting of alkenyl moieties of from 3 to 32 carbon atoms;

$R_2$, $R_3$, and $R_4$ are independently selected from the group consisting of hydrogen, alkyl moieties of from 3 to 32 carbon atoms, and alkenyl moieties of from 3 to 32 carbon atoms; and $R_5$, $R_6$, $R_7$, and $R_8$ are independently selected from the group consisting of hydrogen; unsubstituted phenyl; phenyl substituted with one or more alkyl groups; phenyl substituted with one or more alkoxy groups; phenyl substituted with one or more alkyl amino or aryl amino groups; naphthyl and alkyl substituted naplthyl; straight chain or branched chain alkyl or alkenyl groups containing from one to twenty carbon atoms; and cyclic alkyl groups.

4. The composition of claim 3 wherein $R_5$, $R_6$, $R_7$, and $R_8$ are independently selected from the group consisting of hydrogen; unsubstituted phenyl; phenyl substituted with one or more alkyl groups; phenyl substituted with one or more alkoxy groups; phenyl substituted with one or more alkyl amino or aryl amino groups; naphthyl and alkyl substituted naphthyl; straight chain or branched chain alkyl or alkenyl groups; and cyclic alkyl groups; wherein said alkyl alkoxy, alkyl amino, alkyl substituted naphthyl and alkenyl groups are of from 1 to 20 carbon atoms.

5. A method for inhibiting the oxidation of an organic product selected from the group consisting of lubricants, hydraulic fluids, metal-working fluids, fuels, and polymers comprising adding to said product a stabilizing amount of a compound of the formula:

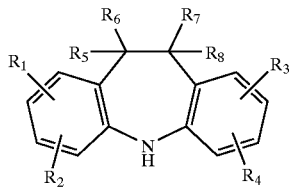

wherein:

$R_1$ is selected from the group consisting of alkenyl moieties of from 3 to 32 carbon atoms;

$R_2$, $R_3$, and $R_4$ are independently selected from the group consisting of hydrogen, alkyl moieties of from 3 to 32 carbon atoms, and alkenyl moieties of from 3 to 32 carbon atoms; and $R_5$, $R_6$, $R_7$, and $R_8$ are independently selected from the group consisting of hydrogen; unsubstituted phenyl; phenyl substituted with one or more alkyl groups; phenyl substituted with one or more alkoxy groups; phenyl substituted with one or more alkyl amino or aryl amino groups; naphthyl and alkyl substituted naphthyl; straight chain or branched chain alkyl or alkenyl groups containing from one to twenty carbon atoms; and cyclic alkyl groups.

6. The method of claim 5 wherein $R_5$, $R_6$, $R_7$, and $R_8$ are independently selected from the group consisting of hydrogen; unsubstituted phenyl; phenyl substituted with one or more alkyl groups; phenyl substituted with one or more alkoxy groups; phenyl substituted with one or more alkyl amino or aryl amino groups; naphthyl and alkyl substituted naphthyl; straight chain or branched chain alkyl or alkenyl groups; and cyclic alkyl groups; wherein said alkyl, alkoxy, alkyl amino, alkyl substituted naphthyl and alkenyl groups are of from 1 to 20 carbon atoms.

7. The compound of claim 1 wherein at least one of $R_2$, $R_3$, and $R_4$ is an alkyl moiety selected from the group consisting of pentyl, hexyl, heptyl, octyl, nonyl, decyl, undecyl, dodecyl, tridecyl, tetrdecyl, pentacyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dontriacontyl, and isomers of the foregoing.

8. The compound of claim 7 wherein at least one of $R_2$, $R_3$, and $R_4$ is nonyl.

9. The compound of claim 1 wherein at least one of $R_2$, $R_3$, and $R_4$ is an alkenyl moiety of from 3 to 32 carbon atoms.

* * * * *